(12) United States Patent
Burtea et al.

(10) Patent No.: US 10,067,092 B2
(45) Date of Patent: Sep. 4, 2018

(54) NOISEMAKER FOR PIPE SYSTEMS

(71) Applicant: Mueller International, LLC, Atlanta, GA (US)

(72) Inventors: Valentin Mircea Burtea, Toronto (CA); Bruce Robertson, Toronto (CA)

(73) Assignee: Mueller International, LLC, Atlanta, GA (US)

( * ) Notice: Subject to any disclaimer, the term of this patent is extended or adjusted under 35 U.S.C. 154(b) by 232 days.

(21) Appl. No.: 14/974,351

(22) Filed: Dec. 18, 2015

(65) Prior Publication Data

US 2017/0176395 A1 Jun. 22, 2017

(51) Int. Cl.
| | |
|---|---|
| *E03B 9/02* | (2006.01) |
| *E03B 7/00* | (2006.01) |
| *G01M 3/00* | (2006.01) |
| *G01N 29/07* | (2006.01) |

(52) U.S. Cl.
CPC ............. *G01N 29/07* (2013.01); *E03B 7/003* (2013.01); *E03B 9/02* (2013.01); *G01M 3/00* (2013.01); *G01N 2291/023* (2013.01); *G01N 2291/0289* (2013.01)

(58) Field of Classification Search
CPC ............. G01N 29/07; G01N 2291/023; G01N 2291/0289; E03B 7/003; E03B 9/02; G01M 3/00
USPC .......................................................... 73/597
See application file for complete search history.

(56) References Cited

U.S. PATENT DOCUMENTS

| | | | | |
|---|---|---|---|---|
| 3,011,754 A | * | 12/1961 | Ander | F16K 1/221 192/58.4 |
| 3,216,244 A | * | 11/1965 | Borchers | G01L 23/02 73/114.68 |
| 3,283,833 A | | 11/1966 | Bodine, Jr. | |
| 4,194,246 A | | 3/1980 | Crist | |
| 4,929,898 A | | 5/1990 | Spies | |
| 5,031,446 A | * | 7/1991 | Saito | G01M 3/243 73/40.5 A |
| 5,526,689 A | | 6/1996 | Coulter et al. | |
| 6,289,723 B1 | * | 9/2001 | Leon | G01M 3/24 73/40.5 A |

(Continued)

FOREIGN PATENT DOCUMENTS

| | | | |
|---|---|---|---|
| CN | 202867884 | * | 10/2012 |
| CN | 2003404430 | * | 1/2014 |

(Continued)

OTHER PUBLICATIONS

Coleman, Matthew Simon; U.S. Patent Application entitled: Determination of Pipe Wall Failure Based on Minimum Pipe Wall Thickness, having U.S. Appl. No. 14/674,851, filed Mar. 31, 2015, 31 pgs.

(Continued)

*Primary Examiner* — J M Saint Surin
(74) *Attorney, Agent, or Firm* — Taylor English Duma LLP

(57) ABSTRACT

A noisemaker system includes a node of an infrastructure system; and a noisemaker connected in fluid communication with the node, the noisemaker including a noisemaker housing defining a noisemaker cavity, and a pulsing device positioned within the noisemaker cavity, the pulsing device configured to contact a fluid within the noisemaker cavity and generate an acoustic signal within the fluid.

14 Claims, 4 Drawing Sheets

(56) References Cited

U.S. PATENT DOCUMENTS

| | | | |
|---|---|---|---|
| 6,453,247 B1* | 9/2002 | Hunaidi | G01M 3/243 |
| | | | 702/51 |
| 6,556,924 B1 | 4/2003 | Kariyawasam et al. | |
| 6,561,032 B1 | 5/2003 | Hunaidi | |
| 7,266,992 B2 | 9/2007 | Shamout et al. | |
| 7,283,913 B2* | 10/2007 | Garnaes | F17D 5/02 |
| | | | 137/458 |
| 7,328,618 B2 | 2/2008 | Hunaidi et al. | |
| 7,475,596 B2 | 1/2009 | Hunaidi et al. | |
| 7,810,378 B2 | 10/2010 | Hunaidi et al. | |
| 7,830,273 B2 | 11/2010 | Twitchell, Jr. | |
| 7,940,189 B2* | 5/2011 | Brown | F16K 37/0075 |
| | | | 340/605 |
| 8,296,083 B2 | 10/2012 | Martin | |
| 8,816,866 B2 | 8/2014 | Day | |
| 8,966,979 B2 | 3/2015 | Amundsen | |
| 9,291,520 B2 | 3/2016 | Fleury, Jr. et al. | |
| 9,541,432 B2 | 1/2017 | Kertesz | |
| 9,651,445 B2 | 5/2017 | McIntyre | |
| 9,670,650 B2 | 6/2017 | Pinney et al. | |
| 9,799,204 B2 | 10/2017 | Hyland et al. | |
| 9,835,592 B2 | 12/2017 | Yusuf et al. | |
| 2001/0032064 A1 | 10/2001 | Araki et al. | |
| 2003/0033870 A1 | 2/2003 | Shah et al. | |
| 2003/0033879 A1 | 2/2003 | Adewumi | |
| 2005/0210960 A1 | 9/2005 | Shamout et al. | |
| 2006/0283251 A1* | 12/2006 | Hunaidi | G01B 17/02 |
| | | | 73/597 |
| 2007/0041333 A1 | 2/2007 | Twitchell | |
| 2009/0250125 A1 | 10/2009 | Howitt | |
| 2012/0125111 A1 | 5/2012 | Groos et al. | |
| 2012/0167688 A1 | 7/2012 | Minachi et al. | |
| 2013/0025375 A1* | 1/2013 | Goldner | G01V 1/226 |
| | | | 73/655 |
| 2013/0036796 A1* | 2/2013 | Fleury, Jr. | G01M 3/00 |
| | | | 73/40.5 R |
| 2013/0211797 A1 | 8/2013 | Scolnicov | |
| 2013/0240093 A1 | 9/2013 | Okada | |
| 2015/0247777 A1* | 9/2015 | Kondou | F17D 5/06 |
| | | | 73/49.1 |
| 2016/0208952 A1 | 7/2016 | Howitt | |
| 2016/0223120 A1 | 8/2016 | Gagliardo | |
| 2016/0252422 A1 | 9/2016 | Howitt | |
| 2016/0290974 A1 | 10/2016 | Coleman | |
| 2017/0248555 A1 | 8/2017 | Yusuf et al. | |

FOREIGN PATENT DOCUMENTS

| | | |
|---|---|---|
| FR | 2754898 | 4/1998 |
| WO | 2010020817 | 2/2010 |
| WO | 2015073313 | 5/2015 |
| WO | 2016160267 | 10/2016 |

OTHER PUBLICATIONS

Hay, Lindsay; "The Influence of Soil Properties on the Performance of Underground Pipelines", Department of Soil Science, The Faculty of Agriculture, The University of Sydney, Aug. 1984, 243 pgs.
Makar, et al.; "Failure Modes and Mechanisms in Gray Cast Iron Pipe", National Research Council Canada, Copyright 2000, 11 pgs.
Muster, et al.; "Life Expectancy of Cement Mortar Linings in Cast and Ductile Iron Pipes", Water Research Foundation, Copyright 2011, 192 pgs.
Rajani, et al.; "Impact of Soil Properties on pipe corrosion: re-examination of traditional conventions", National Research Council Canada, Sep. 2010, 17 pgs.
Rajani, et al.; "Investigation of Grey Cast Iron Water Mains to Develop a Methodology for Estimating Service Life", AWWA Research Foundation, Copyright 2000, 294 pgs.
Yusuf, Shabbir; U.S. Patent Application entitled: Determination of Tuberculation in a Fluid Distribution System having U.S. Appl. No. 14/740,902, filed Jun. 16, 2015, 29 pgs.
Sewerin; Operating Instructions for Combiphon, dated Dec. 10, 2011; 32 pgs.
Yusuf, Shabbir; U.S. Patent Application entitled: External Noise-maker for Pipe Systems having U.S. Appl. No. 15/056,403, filed Feb. 29, 2016, 29 pgs.
Coleman, Matthew Simon; PCT Application entitled: Determination of Pipe Wall Failure Based on Minimum Pipe Wall Thickness having serial No. PCT/US16/20889, filed Mar. 4, 2016, 35 pgs.
Coleman, Matthew, Simon; International Search Report and Written Opinion for PCT Application No. PCT/US2016/020889, filed Mar. 4, 2016, dated Jun. 6, 2016, 14 pgs.
De Silva et al., Condition Assessment and Probabilistic Analysis to Estimate Failure Rates in Buried Pipelines, Thermo Scientific, In: Proceedings of ASTT 5th Conference. Aug. 2002 {Aug. 2002). Retrieved from <https://www.researchgate.net/profile/Magnus_Moglia/publication/236834972_Condition_Assessment_and_Probabilistic_Analaysis_to_Estimate_Failure_Rates_in_Buried_Pipelines/links/00b7d51945e4007c48000000/pdf>, 21 pgs.
Sheppard et al., Cast Iron Fitness for Purpose (FFP)—Final Report, Macaw Engineering, Ltd., Jun. 3, 2015, Retrieved from <http://www.smartemetworks.org/Files/Cast_Iron_Fitness_For_Purpose_{CIFFP)_151214123856.pdf>, 91 pgs.
Yusuf, Shabbir; PCT Application entitled: A Determination of Tuberculation in a Fluid Distribution System, having serial No. PCT/US2016/036856, filed Jun. 10, 2016, 27 pgs.
Coleman, Matthew Simon; Non-Final Office Action for U.S. Appl. No. 14/674,851, filed Mar. 31, 2015, dated Jun. 16, 2017, 50 pgs.
Yusuf, Shabbir; Non-Final Office Action for U.S. Appl. No. 14/740,902, filed Jun. 16, 2015, dated Apr. 27, 2017, 22 pgs.
Yusuf, Shabbir; International Search Report and Written Opinion for serial No. PCT/US2016/036856, filed Jun. 10, 2016, dated Sep. 9, 2016, 10 pgs.
Baik, et al; Article entitled: "Acoustic attenuation, phase and group velocities in liquid-filled pipes: Theory, experiment, and examples of water and mercury", J. Acoust. Soc. Am. 128(5), Nov. 2010, 15 pgs.
Coleman, Matthew Simon; Final Office Action for U.S. Appl. No. 14/674,851, filed Mar. 31, 2015, dated Dec. 15, 2017, 38 pgs.
Yusuf, Shabbir; Issue Notification for U.S. Appl. No. 14/740,902, filed Jun. 16, 2015, dated Nov. 15, 2017, 1 pg.
Yusuf, Shabbir; Non-Final Office Action for U.S. Appl. No. 15/056,403, filed Feb. 29, 2016, dated Jan. 30, 2018, 29 pgs.
Yusuf, Shabbir; International Preliminary Report on Patentability for serial No. PCT/US2016/036856, filed Jun. 10, 2016, dated Dec. 28, 2017, 9 pgs.
Yusuf, Shabbir; Notice of Allowance for U.S. Appl. No. 14/740,902, filed Jun. 16, 2015, dated Aug. 30, 2017, 5 pgs.
Yusuf, Shabbir; Supplemental Notice of Allowability for U.S. Appl. No. 14/740,902, filed Jun. 16, 2015, dated Sep. 15, 2017, 4 pgs.
Coleman, Matthew Simon; International Preliminary Report on Patentability for PCT Application No. PCT/US2016/020889, filed Mar. 4, 2016, dated Oct. 12, 2017, 13 pgs.
Coleman, Matthew Simon; Final Office Action for U.S. Appl. No. 14/674,851, filed Mar. 31, 2015, dated May 21, 2018, 36 pgs.
Yusuf, Shabbir; Written Opinion for Singapore patent application No. 11201710434V, filed Jun. 10, 2016, dated May 31, 2018, 6 pgs.

* cited by examiner

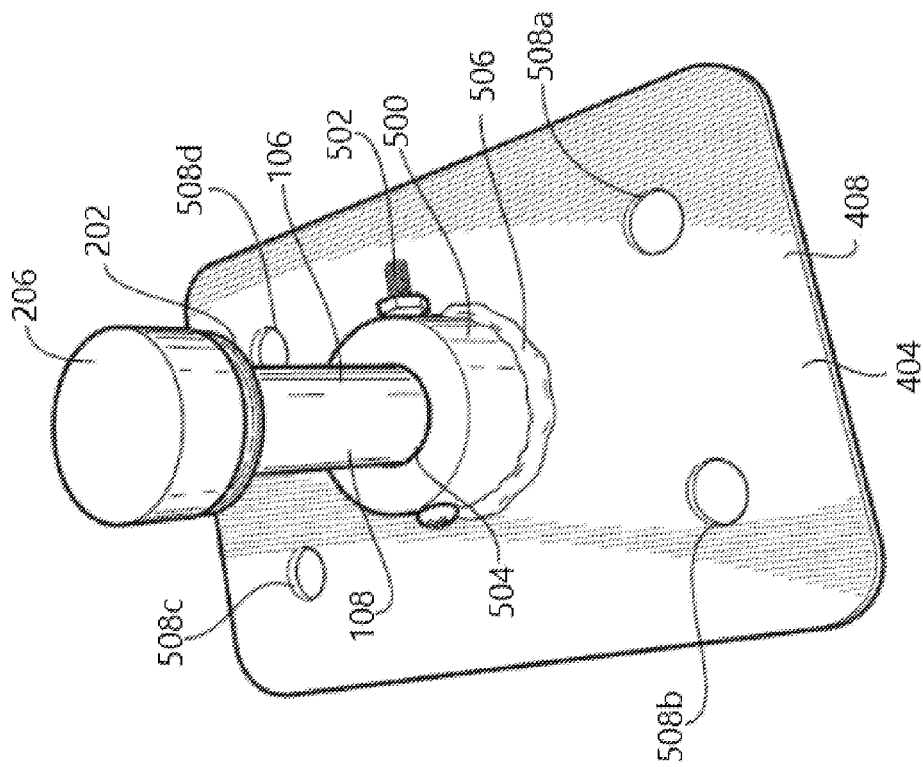
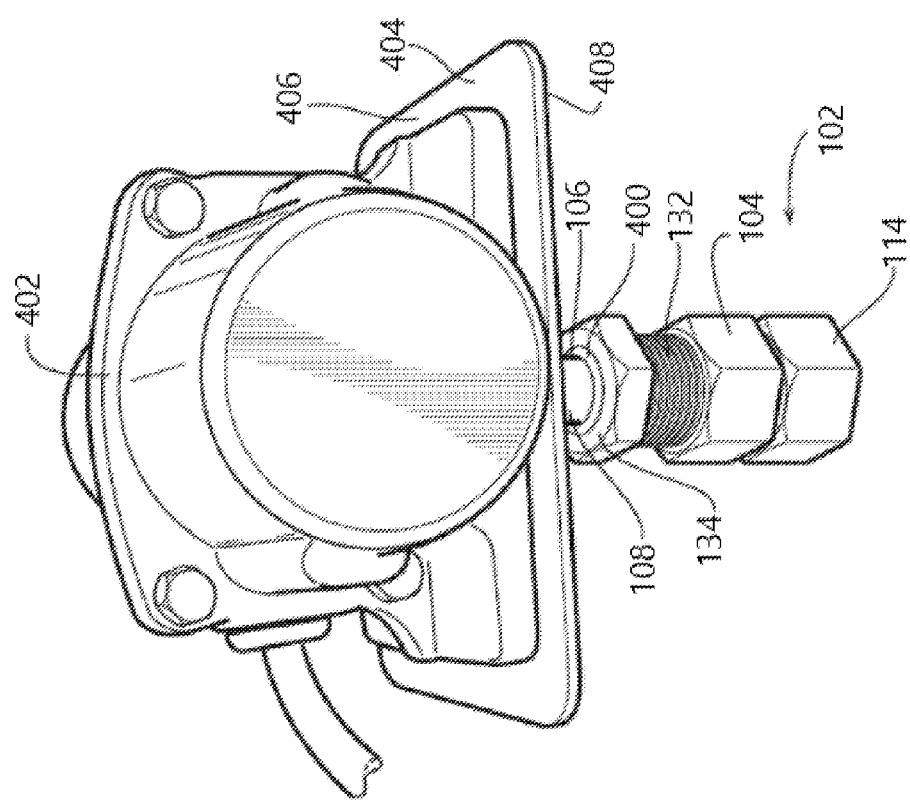

US 10,067,092 B2

NOISEMAKER FOR PIPE SYSTEMS

TECHNICAL FIELD

This disclosure relates to noisemakers. More specifically, this disclosure relates to devices which generate noise in fluid pipe systems.

BACKGROUND

As infrastructure pipe systems, such as those in the water, wastewater, oil, or gas industries, reach the end of their service lives, they tend to leak more, have leaks that are more difficult to find, and have higher risks of catastrophic failure. For example, pipes in the system may lose metal resulting in a reduction in pipe wall thickness, typically as a result of internal and external corrosion. Sustained wall thickness loss eventually causes the pipes to fail. Main breaks, as well as pipe age and material, have historically been the key determinants for selecting pipes to replace or rehabilitate. However, these factors may not be indicative of the current or even future condition of the pipeline because pipes may decay at different rates, even if pipes are the same age and close in physical proximity. Finding these weakened pipes, especially along long lines of underground or otherwise inaccessible pipes, therefore assists in protecting pipe system integrity.

SUMMARY

Disclosed is a noisemaker system including: a node of an infrastructure system; and a noisemaker connected in fluid communication with the node, the noisemaker including a noisemaker housing defining a noisemaker cavity, and a pulsing device positioned within the noisemaker cavity, the pulsing device configured to contact a fluid within the noisemaker cavity and generate an acoustic signal within the fluid.

Also disclosed is a noisemaker including: a noisemaker housing, the noisemaker housing defining a noisemaker cavity, the noisemaker cavity in fluid communication with an infrastructure pipe system; and a pulsing device, the pulsing device positioned within the noisemaker cavity and configured to generate an acoustic signal within a fluid of the infrastructure pipe system.

Also disclosed is a method including: mounting a noisemaker on a node of an infrastructure system, the noisemaker comprising a noisemaker housing defining a noisemaker cavity, and a pulsing device positioned within the noisemaker cavity; and generating an acoustic signal in the fluid by contacting the pulsing device with a fluid within the noisemaker cavity.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

FIG. 4 is a perspective view of the first noisemaker of FIG. 1 with a displacement mechanism including a mounting plate attached to the first noisemaker.

FIG. 5 is a perspective view of a piston of the first noisemaker of FIG. 1 connected to the mounting plate of FIG. 4.

DETAILED DESCRIPTION

Disclosed is a noisemaker and associated methods, systems, devices, and various apparatus. It would be understood by one of skill in the art that the disclosed noisemaker is described in but a few exemplary embodiments among many. No particular terminology or description should be considered limiting on the disclosure or the scope of any claims issuing therefrom.

Noisemakers are devices designed to generate noise in infrastructure piping systems, such as water pipes. In various embodiments, an infrastructure system is a water infrastructure system. The infrastructure system includes various nodes such as pipes, meters, pumps, valves, storage tanks, and various other access or connection points. In various embodiments, a node of the infrastructure system is a fire hydrant. In various embodiments, the generated noise may be used to measure the velocity of sound in the pipe, which may be utilized for pipe wall assessment. In various embodiments, the velocity of sound in the pipe may be indicative of the condition of the pipeline. For example, in various embodiments, an average minimum pipe wall thickness may be determined from the average propagation velocity of sound in the pipe. The propagation velocity of noise may depend on parameters such as the internal diameter and circumferential thickness profile of the pipe, density and bulk modulus of elasticity of the fluid in the pipe, and Young's modulus of elasticity and Poisson's ratio of the pipe wall material. In various embodiments, the propagation velocity, which is usually the average propagation velocity, can be determined by measuring the time delay between acoustic signals measured at two points on a pipe that are a known distance apart, such as at a control valve, fire hydrant, or other point on the pipe, using devices such as hydrophones or vibration sensors. The generated noise may also be utilized to locate a pipe with various listening or sound-measuring equipment. The frequency and regularity of the noise may also need to be adjusted based on the different parameters of the system to obtain better readings.

As described below, a noisemaker is a sound source and generally includes a noisemaker housing and an acoustic mechanism configured to generate an acoustic signal within a fluid, such as a water column. In various embodiments, the acoustic mechanism is housed within the noisemaker housing. In various embodiments, the acoustic mechanism is housed within a noisemaker cavity defined by the noisemaker housing. In various embodiments, the acoustic mechanism is in fluid communication with the water column. The direct fluid communication between the acoustic mechanism and the water column may increase both the clarity and the quality of the acoustic signal generated and may increase the distance that the acoustic signal travels compared to striking an exterior of a pipe.

Figure 1:
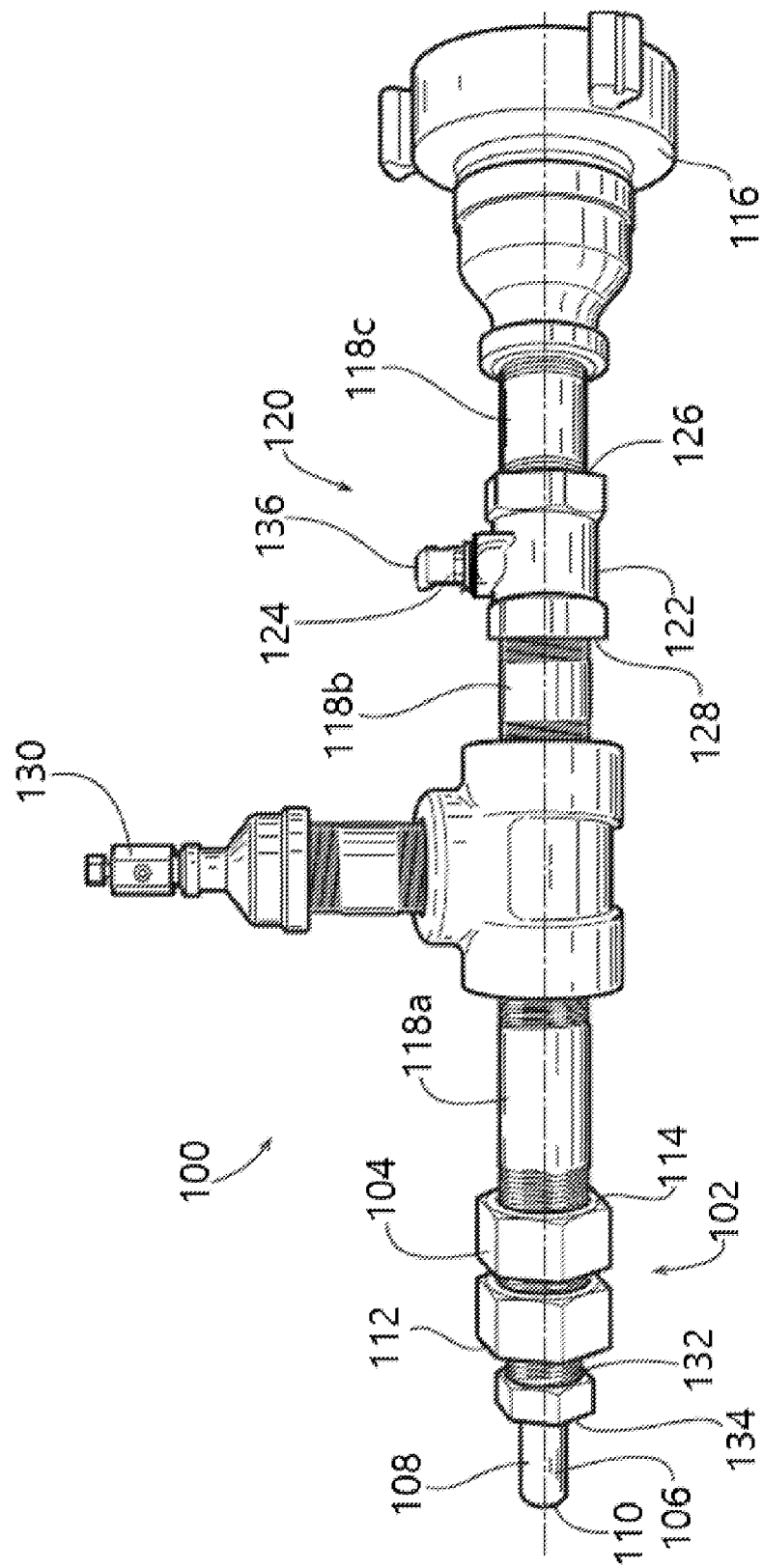
FIG. 1 is a side view of a noisemaker system including a first noisemaker in accordance with one embodiment of the current disclosure.

One embodiment of a noisemaker system 100 is disclosed and described in FIG. 1. The noisemaker system 100 includes a first noisemaker 102.

The noisemaker system 100 is configured to connect to infrastructure piping systems, such as water distribution piping systems, at various nodes within the system, such as at control valves or fire hydrants in water distribution piping systems. In various embodiments, the noisemaker system 100 connects to a node, such as a nozzle on a fire hydrant, through a node adapter 116. In various other embodiments, the noisemaker 102 may directly connect to the node without the use of the node adapter 116. The fire hydrant may be a dry barrel hydrant in various embodiments. In these embodiments, the noisemaker system 100 may be connected to a nozzle of the dry barrel hydrant before a hydrant valve is opened to fill a barrel of the hydrant and the noisemakers 102,302 with water. In various other embodiments, the noisemaker system 100 may be connected to various other access points on a pipe network such as various valves, hydrants, or other access points. The noisemaker system 100 may connect to a wet barrel hydrant in various embodiments.

The first noisemaker 102 is a piston device and includes a piston housing 104 and a piston 106. The piston 106 includes a piston rod 108 and a piston head 200 (shown in FIG. 2). In various embodiments, the piston rod 108 includes a first end 110 and a second end (not shown). The piston rod 108 is connected to the piston head 200 at the second end of the piston rod 108. In various embodiments, the piston rod 108 and piston head 200 are cylindrical and a diameter of the piston head 200 is greater than a diameter of the piston rod 108; however, the shape of the piston rod 108 or piston head 200 should not be considered limiting on the current disclosure as in various other embodiments, the piston rod 108 or piston head 200 may have any desired shape.

The piston housing 104 includes a first end 112 and a second end 114. The piston housing 104 defines a piston cavity (not shown) within the piston housing 104. The piston cavity is substantially continuous from a first opening (not shown) at the first end 112 to a second opening (not shown) at the second end 114. The piston head 200 is contained within the piston cavity of the piston housing 104 and moves within the piston cavity of the piston housing 104 via the piston rod 108.

As shown in FIG. 1, the noisemaker 102 includes a neck 132 connected to the piston housing 104. In various embodiments, the neck 132 includes threading 204 (shown in FIG. 2) as a connection mechanism for securing the neck 132 to the piston housing 104; however, in various other embodiments, other connection mechanisms may be utilized to secure the neck 132 to the piston housing 104. The neck 132 includes a first end 134 and a second end (not shown) and defines a neck cavity (not shown). The neck cavity is substantially continuous from a first opening 400 (shown in FIG. 4) at the first end 134 to a second opening (not shown) at the second end of the neck 132. The neck cavity has a diameter that is less than the diameter of the piston head 200 such that the piston head 200 is stopped by the neck 132 and may not move through the neck cavity. The piston rod 108 extends through the neck cavity such that the first end 110 of the piston rod 108 is positioned exterior to the piston housing 104 and exterior to the neck 132. In various embodiments, fluid, such as water, may flow through the second opening and into the piston cavity. The piston cavity is thus in fluid communication with the rest of the noisemaker system 100 and thereby the piping system.

The noisemaker 102 is configured to connect to an infrastructure piping systems, such as water distribution piping systems, at various nodes, such as at control valves or fire hydrants in water distribution piping systems, through the piston housing 104. In various embodiments, the piston housing 104 connects to a node, such as a nozzle on a fire hydrant, through a node adapter 116. In the present embodiment, the node adapter 116 is a hydrant adapter; however, in various other embodiments, the node adapter 116 may be any suitable node adapter for connecting the piston housing 104 to the infrastructure piping system.

As shown in FIG. 1, in various embodiments, the piston housing 104 is connected to the node adapter 116 through connector pipes 118a,b,c. The shape, location, number, or size of the connector pipes 118a,b,c should not be considered limiting on the current disclosure as the connector pipes 118 may include any desired shape, any desired number of connector pipes 118, and any desired size, and may be positioned at any desired location. Fluid, such as a water column within the infrastructure piping system, may fill the connector piping 118a,b,c and the piston housing 104 when the piston housing 104 is connected, thereby providing the piston head 200 within the piston housing 104 direct access to the water column and placing the piston head 200 in fluid communication with the water column.

Figure 2:
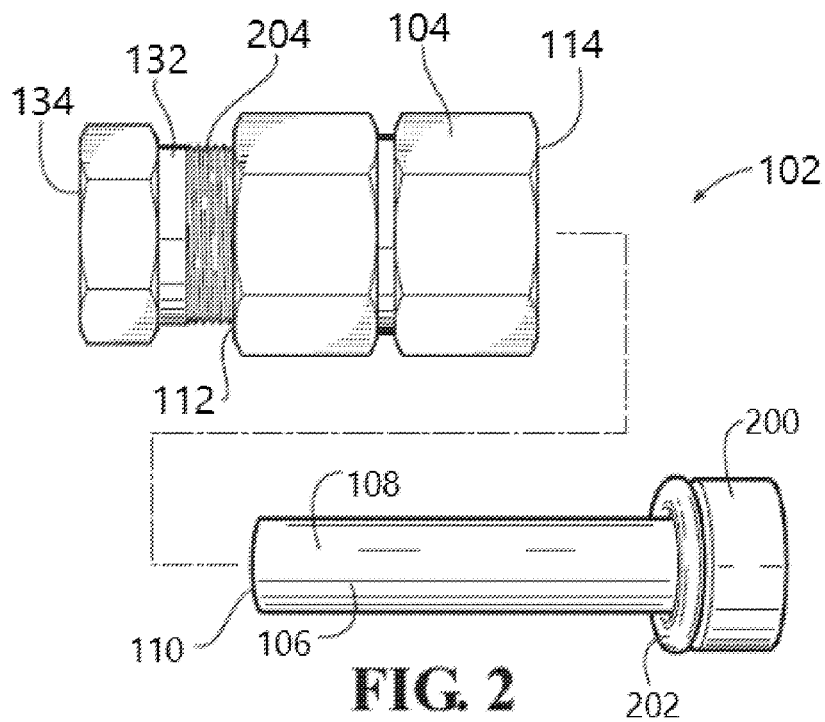
FIG. 2 is a side view of the first noisemaker of FIG. 1 disassembled.

In a fully closed position of the piston 106, the first end 110 of the piston rod 108 is at a maximum distance from the first end 112 of the piston housing 104. In the fully closed position, the piston head 200 may abut against the neck 132 and closes the first opening. As shown in FIG. 2, in various embodiments, the noisemaker 102 includes an O-ring 202 positioned on the piston rod 108 adjacent to the piston head 200. In various embodiments, the O-ring 202 may provide a leak-proof seal between the piston head 200 and the neck 132 when the piston 106 is in the fully closed position. In various other embodiments, various other sealing mechanisms may be utilized instead of the O-ring 202 or in addition to the O-ring 202 such that a seal is formed between the piston rod 108 and the neck 132 when the piston 106 is at intermediate positions less than the fully closed position within the piston housing 104.

Water pressure within the noisemaker system 100 maintains the piston 106 in the fully closed position until the piston rod 108 is displaced through a force applied to the piston rod 108. Displacement of the piston rod 108 displaces the piston head 200 and moves the piston head 200 through the piston cavity of the piston housing 104 away from the first end 112. In various embodiments, the force acting on the piston rod 108 to displace the piston head 200 may be supplied through a tool such as a hammer striking the first end 110 of the piston rod 108, by a vibrator 402 (shown in FIG. 4) connected to the piston rod 108, or various other displacement mechanisms which impact the piston head 200 of the piston 106 to move through the piston housing 104. For example, in various other embodiments, a cam device (not illustrated) may be attached to the noisemaker 102 or at various other locations in the noisemaker system 100. The cam device includes a cam that engages the piston rod 108 to deliver pulses of force to the piston rod 108 at regular or irregular intervals.

In a displaced position of the piston 106, the first end 110 of the piston rod 108 is at a distance from the first end 112 of the piston housing 104 less than the maximum distance of the fully closed position. After the piston 106 is displaced, the water pressure within the noisemaker system 100 returns the piston 106 in the fully closed position until the piston rod 108 is displaced again. In various embodiments, the piston 106 may be displaced at varying intervals. The time intervals at which the piston 106 is displaced may be at regular intervals or irregular intervals.

The piston head 200 is displaced within the piston housing 104 such that the piston head 200 contacts and directly displaces water within the piston housing 104 and thereby within the infrastructure piping system. Displacement of the piston head 200 to directly displace water within the piston housing 104 creates a pressure pulse, or an acoustic signal, in the water column. In various embodiments, the force of the displacement of the piston head 200 is controlled to vary the strength of the acoustic signal. In various embodiments, the frequency of the displacement of the piston head 200 is controlled to vary the frequency of the acoustic signal. The acoustic signal created by the displacement may be utilized for pipe wall assessment and determining the locations of pipes in various embodiments.

As shown in FIG. 1, the noisemaker system 100 includes an access valve 120, which may be selectively opened or closed to put the noisemaker 102 in contact with the water column. The access valve 120 includes a valve housing 122 and a valve (not shown). The valve housing 122 includes a first end 126 defining an inlet and a second end 128 defining an outlet. The valve housing 122 defines a valve cavity which is substantially continuous from the inlet to the outlet of the valve housing 122 to allow fluid flow through the valve housing 122. The valve housing 122 is connected to the node adapter 116 through the connector pipe 118c. The water column within the infrastructure piping may flow through the connector pipe 118c and the valve housing 122 when the valve housing 122 is connected, thereby providing the valve within the valve housing 122 direct access to the water column.

The valve is housed in the valve housing 122 and is actuated by a stem 124. In various embodiments, the stem 124 is positioned in the valve cavity and is connected to the valve. The stem 124 can be rotated to actuate the valve within the valve housing 122 and to open or close the valve selectively. In various embodiments, the stem 124 includes a handle 136 to rotate the stem 124 and thereby actuate the valve within the valve housing 122 between an open position and a closed position. In the present embodiment, the valve is a ball valve having a ball connected to the stem 124. The ball defines a bore therethrough through which fluid may pass when the ball is rotated to the open position, but blocks fluid flow when the ball is rotated to the closed position. Opening the access valve 120 may allow the water or fluid to flow at full force through the valve housing 122 and closing the access valve 120 may abruptly interrupt the flow of the water; however, in various other embodiments, the valve may be various other types of valves, such as a butterfly valve.

As shown in FIG. 1, in various embodiments, the noisemaker system 100 includes a purge valve 130. In various embodiments, the purge valve 130 is included to remove air or other gases from the noisemaker system 100 prior to activation of the noisemaker 102, as well as debris that can interfere with the operation of the noisemaker system 100. In various embodiments, if air is in the noisemaker system 100, displacement of the piston 106 of the noisemaker 102 would compress the air and as a result, reduce the magnitude of the pressure pulse generated in the water column when the piston 106 directly displaces the water. Air present in the noisemaker system 100 may act as a cushion to reduce the effect of the pressure pulse.

FIG. 2 shows the first noisemaker 102 with the piston 106 removed from the piston housing 104 to show the piston head 200 and O-ring 202 of the piston 106.

Figure 3:
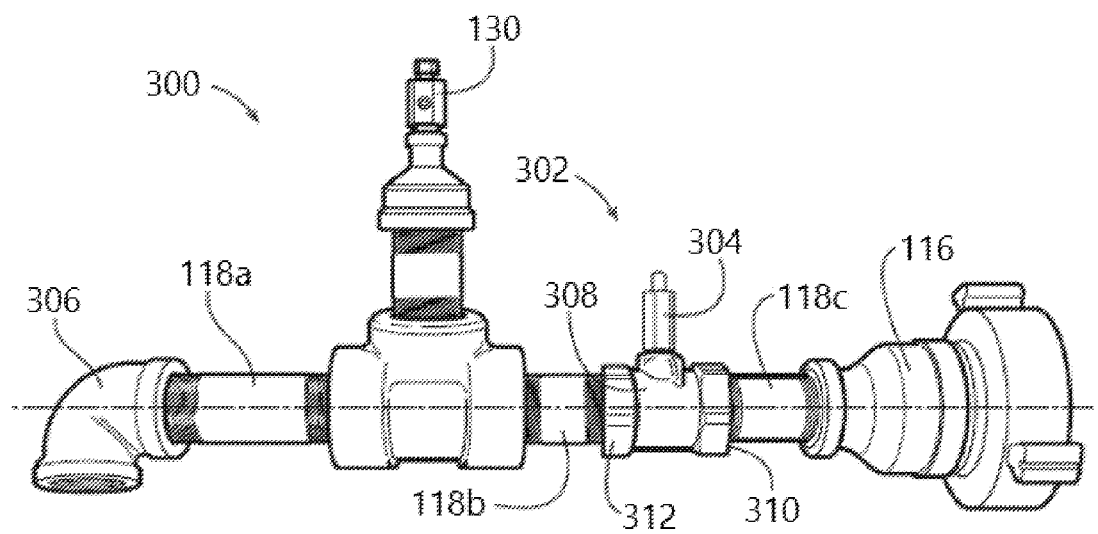
FIG. 3 is a side view of a noisemaker system in accordance with another embodiment of the current disclosure, the noisemaker system including a second noisemaker.

FIG. 3 shows another embodiment of a noisemaker system 300. As shown in FIG. 3, the noisemaker system 300 includes a second noisemaker 302. The second noisemaker 302 includes a valve housing 308 and a valve (not shown). The valve housing 308 is similar to the valve housing 122 and includes a first end 310 defining an inlet and a second end 312 defining an outlet. The valve housing 308 defines a valve cavity which is substantially continuous from the inlet to the outlet of the valve housing 308 to allow fluid flow through the valve housing 308. The valve housing 308 is connected to the node adapter 116 through the connector pipe 118c. The water column within the infrastructure piping may flow through the connector pipe 118c and the valve housing 308 when the valve housing 308 is connected, thereby providing the valve within the valve housing 308 direct access to the water column.

The valve is housed in the valve housing 308 and is actuated by a stem (not shown). In various embodiments, the stem is positioned in the valve cavity and is connected to the valve. The stem can be rotated to actuate the valve within the valve housing 308 and to open or close the valve selectively. In various other embodiments, a variable speed motor (not shown) is connected to the stem to rotate the stem and thereby actuate the valve. The opening and closing of the valve creates a pulsating water flow which generates noise, or an acoustic signal, as a pulse in the water column. The rate at which the valve opens and closes can be controlled to vary the frequency of the pulsating flow and thereby the frequency of the acoustic signal. In various embodiments, the valve may be opened and closed at regular time intervals or irregular time intervals. In various other embodiments, the valve is not continuously opened and closed. Instead, in various embodiments, a closed valve may be rapidly opened, may remain in a fully open position for a period to allow water flow through the valve housing 308, and then the valve may be closed rapidly and remain fully closed for a period of time. These embodiments including leaving the valve open for a period of time and closed for a period of time and may provide for a more dramatic flow pulsation. A cam device including a cam may be utilized in these embodiments to engage the stem such that the valve remains open for a period of time and closed for a period of time. In various other embodiments, a cam device may be utilized to continuously open and close the valve within the valve housing 308.

In the present embodiment, the valve is a butterfly valve having a rotatable disc connected to the stem; however, in various other embodiments, the valve may be various other types of valves, such as a ball valve, which may allow the water or fluid to flow at full force through the valve housing 308 and then abruptly interrupt the flow of the water. In various embodiments, the butterfly valve is rotated through the variable speed motor connected to the stem. In various other embodiments, various other displacement mechanisms configured to rotate the valve may be utilized. The rotational speed of the butterfly valve is controlled to vary the frequency of the pulsating flow.

As shown in FIG. 3, in various embodiments, the noisemaker 302 includes an adapter 304, which is connected to the stem of the noisemaker 302. In various embodiments, the adapter 304 is utilized by the variable speed motor to rotate the stem. In the present embodiment, the adapter 304 is a drill adapter for attachment to and activation by a drill, such as a cordless drill, to rotate the stem. As shown in FIG. 3, the noisemaker system 300 includes a pipe joint 306 connected to the connector pipe 118a. The pipe joint 306 may be connected to various other components of the piping system such as other pipes, other valves, faucets, or other components of the piping system, or may not be connected to any other components of the pipe system and simply vent to an exterior of the pipe system, such as a street or ground surface adjacent to a fire hydrant. The second noisemaker 302 expels fluid from the noisemaker system 300 at intervals and the fluid exits the noisemaker system 300 through the joint 306. The disclosure of the pipe joint 306 should not be considered limiting on the current disclosure as in various other embodiments, any suitable pipe joint or other piping system component may be utilized, or the pipe joint 306 might not be present and the fluid exits from the noisemaker system 300 from the connector pipe 118a.

In the current embodiment, the noisemaker system 300 is a modification of the noisemaker system 100 wherein the noisemaker 102 is detached and replaced by the joint 306. The pipe joint 306 may be provided as an accessory to the noisemaker system 100 to provide a downward-facing outlet for expelling fluid with the noisemaker 302. The pipe joint 306 and the noisemaker 102 are both removable and interchangeable as desired.

FIG. 4 shows the first noisemaker 102 connected to the vibrator 402. In various embodiments, the vibrator 402 is utilized to generate a force to act on the piston rod 108 and displace the piston rod 108 and piston head 200 within the piston cavity of the piston housing 104. In various embodiments, the speed, frequency, and force of the vibrator may be adjustable.

As shown in FIG. 4, the vibrator 402 may be attached to a top side 406 of a mounting plate 404 through an attachment mechanism such as welding, adhesives, nuts and bolts, screws, or various other attachment mechanisms. The mounting plate 404 includes a connector 500 (shown in FIG. 5) attached to a bottom side 408 of the mounting plate 404 such that the mounting plate 404 may connect to the piston rod 108. The connector 500 may include a securing mechanism 502 (shown in FIG. 5), such as threading, pins, bolts, hooks, or various other securing mechanisms to secure the piston rod 108 to the connector 500.

As shown in FIG. 5, in various embodiments, the connector 500 is a cylinder defining a connector bore 504. The shape of the connector 500 should not be considered limiting as in various other embodiments, the connector 500 may have any desired shape. In the present embodiment, the connector 500 is connected to the mounting plate 404 through welding 506; however, in various other embodiments, the connector 500 may be attached to the mounting plate 404 through various other attachment mechanisms such as adhesives, nuts and bolts, screws, or various other attachment mechanisms, or may be formed integrally with the mounting plate 404, for example by molding or machining. The connector bore 504 may have a diameter sized to receive the piston rod 108 into the connector bore 504.

The piston rod 108 may define a piston pin bore (not shown) extending transversely through the piston rod 108 and the connector 500 may define a connector pin bore (not shown) extending transversely through the connector 500. As described above in various embodiments, the connector 500 includes the securing mechanism 502, which in the present embodiment is a nut and bolt; however, in various other embodiments, the securing mechanism 502 is any suitable securing mechanism. In various embodiments, the securing mechanism 502 is positioned through the piston pin bore and the connector pin bore and secured such that the piston rod 108 is secured and attached to the connector 500. Securing the piston rod 108 to the connector 500 retains the piston rod 108 within the connector bore 504 and thereby attaches the piston rod 108 to the mounting plate 404.

As shown in FIG. 5, in various embodiments, the mounting plate 404 defines a plurality of mounting bores 508 extending through the mounting plate 404 from the top side 406 to the bottom side 408. In the present embodiment, the mounting plate 404 defines four mounting bores 508a,b,c,d; however, the number of mounting bores 508 should not be considered limiting as in various other embodiments, any desired number of mounting bores 508, including one or no mounting bores 508, may be utilized. In various embodiments, the mounting bores 508 are provided to receive a securing mechanism (not shown) through the mounting bores 508 to secure the vibrator 402 to the mounting plate 404. In various other embodiments, the vibrator 402 may be secured to the mounting plate 404 through any suitable securing mechanism including, but not limited to, nuts and bolts, screws, pins, hooks, adhesives, welding, and various other securing mechanisms. In various embodiments, the vibrator 402 is a variable speed vibrator such that the rate at which the piston 106 is displaced within the piston housing 104 can be controlled to vary the frequency of the pressure pulse and thus the frequency of the acoustic signal.

Figure 6:
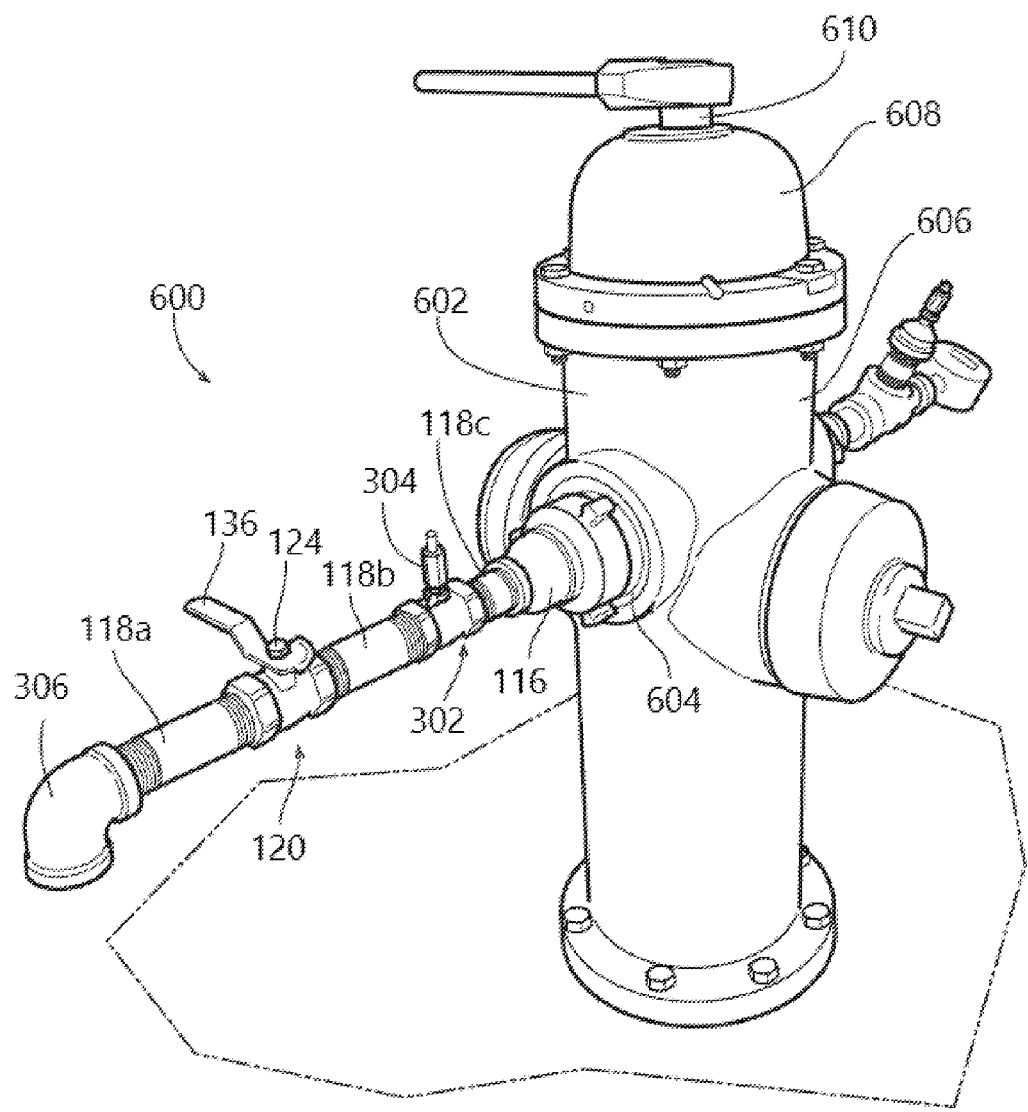
FIG. 6 is a perspective view of a noisemaker system in accordance with another embodiment of the current disclosure, the noisemaker system including the second noisemaker of FIG. 3.

FIG. 6 shows another embodiment of a noisemaker system 600 connected to a nozzle 604 on a fire hydrant 602, through the node adapter 116. As shown in FIG. 6, the noisemaker system 600 includes the second noisemaker 302 and the access valve 120. In various embodiments, the access valve 120 may be in a fully open position to permit fluid flow through the pipe joint 306 or in a partially open position to permit reduced fluid flow through the pipe joint 306 while the second noisemaker 302 is being used. In the current embodiment, the hydrant 602 is a dry-barrel fire hydrant having a hydrant body 606 and a bonnet 608 connected to a top end of hydrant body 606. A hydrant shoe (not shown) is connected to a bottom end of the hydrant body 606 and may be connected to a water supply pipe or any other fluid supply pipe. In various embodiments, hydrant 602 may be other types of fire hydrants, such as a wet-barrel fire hydrant, and the disclosure of a dry-barrel fire hydrant should not be considered limiting. In the current embodiment, an operating nut 610 is mounted on the bonnet and has a threaded connection with a stem (not shown). The stem is connected to a main valve (not shown) in the hydrant 602 such that operation of the operating nut 610 opens the main valve to allow water to flow from the water supply pipe to the hydrant body 606 or closes the main valve to discontinue water flow from the water supply pipe to the hydrant body 606. The main valve can be opened and closed by turning the operating nut 610 to actuate the main valve between an open position and a closed position.

Any of the noisemaker systems 100,300,600 may be open looped systems or closed loop systems with feedback control. Although the discussion below is directed towards the noisemaker system 100 with the noisemaker 102, the discussion is equally applicable to the noisemaker systems 300,600 and the second noisemaker 302. When the noisemaker system 100 is an open loop system, the noisemaker system 100 does not receive feedback to make adjustments to the system.

When the noisemaker system 100 is closed loop systems, the noisemaker system 100 includes acoustic sensors in wired or wireless communication with a controller device controlling the noisemaker 102. The noisemaker system 100 is connected to a node of the pipe network and an acoustic sensor is placed on the same pipe network but at a different node located in proximity to the noisemaker system 100. The number of acoustic sensors should not be considered limiting as in various embodiments, any desired number of acoustic sensors may be utilized. The acoustic sensors and noisemaker system 100 may be in bi-directional wireless communication through a controller. In various other embodiments, the acoustic sensors and noisemaker system 100 may be in bi-directional wired communication. The controller may utilize the feedback from the sensors to adjust the frequency pattern of the acoustic signal generated by the noisemaker 102 as different pipe segments may be responsive to different frequencies due to pipe composition, pipe location, or various other aspects of the pipe. In various other embodiments, the controller may be omitted.

An objective of the noisemaker systems 100,300,600 is to inject sound into a fluid-filled pipe in order to determine the propagation speed of the acoustic waves in the fluid-pipe system. To estimate the propagation speed, the sound may be sensed by multiple sensors, such as at least two sensors, placed at various locations along the pipe. Various sensing technologies may be used for the sensors, including but not limited to piezoelectric accelerometers placed on a pipe surface, hydrophones placed in the water column, or electromagnetic sensors to measure the radial velocity of the pipe wall. Based on the distances between sensors, the propagation speed of acoustic waves and the propagation delay of the signal observed at multiple locations along the pipe may be determined.

A method of adjusting the frequency pattern of the acoustic signal generated by the noisemakers 102,302 using the acoustic sensors is also provided. The method is described with reference to the noisemaker system 100, however, the discussion is equally applicable to noisemaker systems 300,600.

In a calibration step according to various embodiments of the current disclosure, the noisemaker system 100 is used to determine the best excitation frequency for the acoustic signal generated by the noisemaker system 100. The noisemaker 102, the noisemaker 302, or both noisemakers 102, 302 are activated to excite a wide frequency range of acoustic signals. For example, various types of excitations may include frequency sweeps, white noise, multiple tones, and impulses. Using the acoustic sensor (or sensors) placed on the same pipe network as the noisemaker system 100 and in proximity to the noisemaker system 100, the controller device or a user may record the acoustic signal generated and estimate a power spectral density (PSD), which describes the distribution of signal energy over frequency. Power spectral density is also referred to as a spectrum. The largest peak in the spectrum may indicate the best carrier frequency. In various embodiments, the identification of the best carrier frequency may further be limited to a specific frequency range based on various pipe characteristics, such as pipe material composition or pipe size.

A pseudo-random binary sequence that has ideal auto-correlation properties is then generated. A pseudo-random binary sequence includes N samples, each sample taking only one of two values (e.g. 1 or −1). The auto-correlation function of the pseudo-random binary sequence has a single peak (for k=0), while all other values are 1 or −1, and may be represented by the following formula:

$$c(k) = \sum_{i=1}^{N} a_i a_{i+k}$$

$$C(0) = N$$

$$C(k0) = 1 \text{ or } -1 \text{ for } k < 0 \text{ or } k > 0$$

In various embodiments, the sequence is generated with a linear shift register. The shift register may use a polynomial such as $p(x)=x^{31}+x^{28}+1$ for sequence generation, though other polynomials may be used in various other embodiments and the disclosure of the polynomial $p(x)=x^{31}+x^{28}+1$ should not be considered limiting on the current disclosure. In various embodiments, the ideal auto-correlation properties may provide a good estimation of the propagation velocity of the acoustic signal. The pseudo-random binary sequence is then modulated to the carrier frequency to generate an excitation sequence using various modulation schemes including, but not limited to, phase shift keying, frequency shift keying, or amplitude shift keying. The phase shift key may be represented by multiplying the pseudo-random binary sequence with a sinusoidal signal with a carrier frequency fc. Frequency shift keying and amplitude shift keying mean encoding a pseudo random sequence over multiple tones or multiple pulses, respectively. The pseudo-random binary component provides the excitation sequence with a good estimation of propagation velocity and the carrier frequency component provides the excitation sequence with good energy propagation over a long distance.

The excitation sequence may be utilized by the noisemaker 102, noisemaker 302, or both noisemakers 102,302 of the noisemaker system 100 to generate an acoustic signal with the desired frequency and regularity. For example, in various embodiments including a cam device connected to a noisemaker 102, the excitation sequence may be implemented by controlling the rotational speed of the cam. Controlling the rotational speed controls the frequency at which the cam engages the piston rod 108 to deliver pulses of force to the piston rod 108 and thereby controls the frequency of the pressure pulses generated by the noisemaker 102. In various other examples, the excitation sequence may include a burst-pause scheme or alternative frequencies such that the noisemaker system 100 generates a series of pulses with a variable delay. The disclosure of the cam device should not be considered limiting as in various other embodiments, the acoustic signal may be generated through various other mechanisms.

In various embodiments, a timing device may be attached to both the sensor and the noisemaker system, and a processor may be present to perform a cross-correlation over a known distance and determine the propagation velocity, giving an estimate of the average minimum wall thickness of the pipe.

The generated acoustic signal with the desired frequency and regularity may be utilized by an operator can perform a signal correlation over a known distance. The operator may correlate the signal acquired from one or multiple sensors with the excitation. Through the signal correlation, the operator may determine the propagation velocity of the acoustic signal and an estimate of the average minimum wall thickness of the pipe. In various embodiments, signal cross-correlation may be utilized to determine the propagation delay from the source to the sensor. This information may be processed to measure the propagation velocity and estimate the pipe wall thickness in various embodiments.

The piston housing 104 and the valve housing 122 are two examples of noisemaker housings, and the piston cavity and the valve cavity are two examples of noisemaker cavities, though other types of noisemaker housings and noisemaker cavities may be present in various other embodiments.

In various embodiments, any of the noisemaker systems 100,300,600 may include both noisemakers 102,302 or only one of the noisemakers 102,302. In embodiments where both noisemakers 102,302 are included, at least the piston 106 is detached and removed from the noisemaker system prior to actuation of the second noisemaker 302 to create an outlet for fluid flow from the noisemaker system 100 during use of the second noisemaker 302. The first noisemaker 102 may also be detached and removed from the noisemaker system to create an outlet. However, in various other embodiments, another outlet is provided on the noisemaker system 100 and therefore neither the piston 106 nor the first noisemaker 102 are detached or removed from the noisemaker system 100. For example, in various other embodiments, the noisemaker system is Y-shaped with the first noisemaker 102 positioned on one branch and the second noisemaker 302 is positioned on a second branch. In another example, the purge valve 130 may be used to expel fluid from the system with the second noisemaker 302 or the first noisemaker 102.

One should note that conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment. Directional references such as "up," "down," "top," "left," "right," "front," "back," and "corners," among others are intended to refer to the orientation as shown and described in the figure (or figures) to which the components and directions are referencing.

It should be emphasized that the above-described embodiments are merely possible examples of implementations, merely set forth for a clear understanding of the principles of the present disclosure. Many variations and modifications may be made to the above-described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A noisemaker system comprising:
    a node of an infrastructure system; and
    a noisemaker connected in fluid communication with the node, the noisemaker comprising:
        a noisemaker housing defining a noisemaker cavity, and
        a pulsing device positioned within the noisemaker cavity, the pulsing device configured to contact a fluid within the noisemaker cavity and generate an acoustic signal within the fluid,
    wherein the noisemaker housing is a piston housing and the noisemaker cavity is a piston cavity, and
    wherein the pulsing device is a piston comprising a piston rod having a first end and a second end, wherein the first end of the piston rod is positioned exterior to the piston cavity, and wherein the second end of the piston rod is connected to a piston positioned within the piston cavity.

2. The noisemaker system of claim 1, further comprising a purge valve in fluid communication with the noisemaker, the purge valve configured to remove air from the noisemaker system.

3. The noisemaker system of claim 1, wherein the infrastructure system is a water infrastructure system, and wherein the node is a fire hydrant.

4. The noisemaker system of claim 1, wherein the piston includes an O-ring positioned on the piston rod between the first end and the piston, and wherein the O-ring is positioned within the piston cavity.

5. The noisemaker system of claim 1, further comprising a displacement mechanism configured to displace the piston within the piston cavity.

6. The noisemaker system of claim 1, further comprising an adapter connected to the node, wherein the noisemaker is connected to the node via the adapter.

7. A noisemaker comprising:
    a noisemaker housing, the noisemaker housing defining a noisemaker cavity, the noisemaker cavity in fluid communication with an infrastructure pipe system; and
    a pulsing device, the pulsing device positioned within the noisemaker cavity and configured to generate an acoustic signal within a fluid of the infrastructure pipe system,
    wherein the noisemaker housing is a piston housing and the noisemaker cavity is a piston cavity, and
    wherein the pulsing device is a piston, wherein the piston includes a piston rod having a first end and a second end, wherein the first end of the piston rod is positioned exterior to the piston cavity, and wherein the second end of the piston rod is connected to a piston positioned within the piston cavity.

8. The noisemaker of claim 7, further comprising a displacement mechanism configured to displace the piston within the piston cavity.

9. The noisemaker of claim 8, wherein the displacement mechanism is an adjustable speed and adjustable force vibrator.

10. A method comprising:
    mounting a noisemaker on a node of an infrastructure system, the noisemaker comprising:
        a noisemaker housing defining a noisemaker cavity, and
        a pulsing device positioned within the noisemaker cavity;
    generating an acoustic signal in a fluid within the noisemaker cavity by contacting the pulsing device with the fluid;
    recording the acoustic signal generated by the pulsing device;
    estimating a power spectral density; and
    determining a carrier frequency based on the power spectral density.

11. The method of claim 10, further comprising:
generating a pseudo-random binary sequence;
modulating the pseudo-random binary sequence to the carrier frequency to generate an excitation sequence; and
generating a second acoustic sign in the fluid with the pulsing device based on the excitation sequence.

12. The method of claim 10, wherein the noisemaker housing is a piston housing and the noisemaker cavity is a piston cavity, wherein the pulsing device is a piston comprising a piston rod having a first end and a second end, wherein the first end of the piston rod is positioned exterior to the piston cavity, wherein the second end of the piston rod is connected to a piston positioned within the piston cavity, and wherein generating the acoustic signal comprises moving the piston rod within the piston cavity.

13. The method of claim 10, wherein the noisemaker housing is a valve housing and the noisemaker cavity is a valve cavity, wherein the pulsing device is a valve, wherein the valve is positioned within the valve cavity, and wherein generating the acoustic signal comprises rotating the valve within the valve cavity.

14. A method comprising:
mounting a noisemaker on a node of an infrastructure system, the noisemaker comprising:
a noisemaker housing defining a noisemaker cavity, and
a pulsing device positioned within the noisemaker cavity; and
generating an acoustic signal in a fluid within the noisemaker cavity by contacting the pulsing device with the fluid,
wherein the noisemaker housing is a piston housing and the noisemaker cavity is a piston cavity, wherein the pulsing device is a piston comprising a piston rod having a first end and a second end, wherein the first end of the piston rod is positioned exterior to the piston cavity, wherein the second end of the piston rod is connected to a piston positioned within the piston cavity, and wherein generating the acoustic signal comprises moving the piston rod within the piston cavity.

* * * * *